United States Patent [19]

Stenlake et al.

[11] 4,179,507
[45] Dec. 18, 1979

[54] QUARTERNARY AMMONIUM COMPOUNDS

[75] Inventors: John B. Stenlake, Glasgow, Scotland; Roger D. Waigh, Wilmslow, England; George H. Dewar, Bath, England; John Urwin, South Shields, England; Nirmal C. Dhar, Glasgow, Scotland

[73] Assignee: Burroughs Wellcome Co., Research Triangle Park, N.C.

[21] Appl. No.: 749,174

[22] Filed: Dec. 9, 1976

[30] Foreign Application Priority Data

Dec. 10, 1975 [GB] United Kingdom ............... 50589/75
Oct. 29, 1976 [GB] United Kingdom ............... 45028/76

[51] Int. Cl.² .................. A61K 31/47; C07D2, 17/10
[52] U.S. Cl. .................................... 424/258; 546/140; 424/260
[58] Field of Search ............... 424/260, 258; 260/285, 260/286 Q, 289 D; 546/140

[56] References Cited

U.S. PATENT DOCUMENTS 3,004,031  10/1961  Taylor et al. .................... 260/289 D

OTHER PUBLICATIONS

Ger et al., Comp. Gen. Pharmac., (1971), 2, pp. 225-246.
Danilou et al., Br. J. Pharmac., (1972), 44, pp. 765-778.
Mednikyan et al., Chemical Abstracts, (1969), 71, 111205f.

Primary Examiner—Paul M. Coughlan, Jr.

[57] ABSTRACT

Compounds of formula (I):

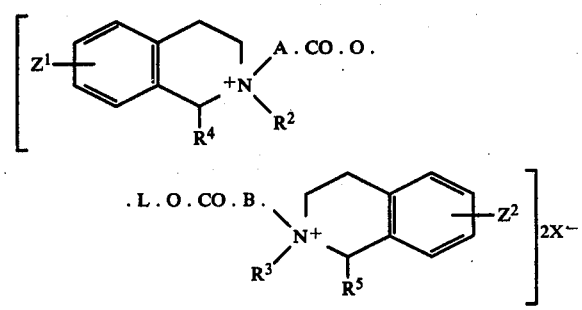

wherein
$Z^1$ and $Z^2$ are the same or different and each represents a methylenedioxy substituent, or up to three methoxy substituents;
$R^2$ and $R^3$ are the same or different and each is alkyl having 1-3 carbon atoms, prop-2-enyl or prop-2-ynyl;
$R^4$ and $R^5$ are the same or different and each is a benzyl or phenethyl group wherein the phenyl ring is optionally substituted by one or more of halogen, alkoxy having 1 to 3 carbon atoms and methylenedioxy;
A and B are the same or different and each is an alkylene radical containing 1,2, or 3 carbon atoms;
L is an alkylene chain having from 2 to 12 carbon atoms or is a group —$L^1.O.L^2$— wherein each of $L^1$ and $L^2$ is alkylene having at least two carbon atoms and taken together $L^1$ and $L^2$ having up to 11 carbon atoms; and
$X^-$ is an anion;

may be used to effect neuromuscular paralysis in mammals.

43 Claims, No Drawings

QUARTERNARY AMMONIUM COMPOUNDS

The present invention relates to heterocyclic compounds with useful biological properties, the synthesis of the compounds, and pharmaceutical compositions containing them.

The heterocyclic compounds are a series of isoquinoline derivatives having pharmacological properties which make them useful as neuromuscular blocking agents (or as they are often called 'muscle relaxants'). Such agents produce paralysis of skeletal muscles by interfering with the neuro-humoral transmission process involving acetylcholine; and some such compounds are widely used during major surgical operations.

One class of muscle relaxants acts by inhibiting or reducing the depolarisation of the motor end plate whereas others act by producing a prolonged depolarisation.

Depolarising agents suffer from a number of disadvantages. They are not antagonised by anticholinesterase drugs and the latter in fact may intensify the depolarisation process. They may also give rise postoperatively to muscle pains and cramps, probably due to initial muscle contractions or fasciculations.

Amongst the other type of blocking agents which inhibit depolarisation are d-tubocurarine, gallamine, and pancuronium. This type of neuromuscular blocking agent has also been referred to as the competitive type because it is thought to compete with acetylcholine at the muscle and plate and prevent its depolarisation. The overall effect of the competitive action is that the muscle remains in the relaxed state and a flaccid paralysis occurs. d-Tubocurarine, pancuronium and gallamine give rise to paralysis of fairly long duration and the rate of recovery is invariably slow. The anticholinesterase agents neostigmine, edrophonium and physostigmine can be used to antagonise paralysis of d-tubocurarine, pancuronium and gallamine and are widely used in anaesthetic practice.

A serious disadvantage of the competitive blocking agents is their effect upon autonomic mechanisms. Tubocurarine blocks the autonomic ganglia causing bradycardia and hypotension whereas gallamine and pancuronium cause vagal blockade resulting in tachycardia and hypertension.

It would be advantageous therefore to provide a series of potent neuromuscular blocking agents which would combine some of the advantages of the known agents of each type without having all of the disadvantages, and in particular a separation between neuromuscular paralysing activity and the effects upon autonomic mechanisms.

A number of isoquinoline derivatives are known to have neuromuscular blocking activity and amongst such substances are a series of diesters related in structure to the compounds of the present invention. These prior compounds showed "considerable variation in {the} pharmacological activity." (J. M. Z. Gladych and E. P. Taylor, J. Chem. Soc. (1962), 1481–1487). One of these diesters, designated γ-oxalolaudonium of formula A below, "appeared to be worthy of further examination" (R. T. Brittain et al., Brit. J. Pharmacol. (1961), 17, 116–123), though "it was of relatively low potency in animals" and was subsequently shown "to be too weak in human volunteers to be of any value in anaesthesia." (Gladych, p. 1483).

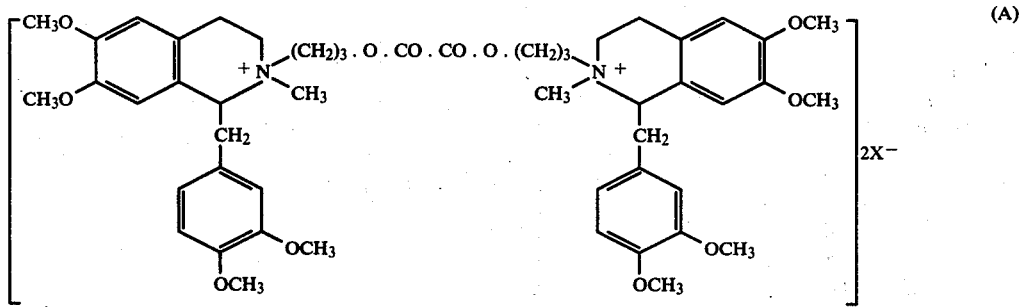

(A)

The present invention provides isoquinolinium compounds of general formula (I) which produce neuromuscular paralysis, by a non-depolarising mechanism of a relatively short duration with a minimal effect upon cardiovascular and autonomic mechanisms.

In formula (I):

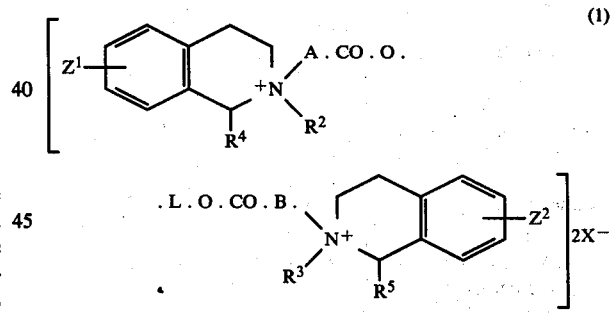

(I)

$Z^1$ and $Z^2$ are the same or different and each represents a methylenedioxy substituent, or up to three methoxy substituents;

$R^2$ and $R^3$ are the same or different and each is alkyl having 1 to 3 carbon atoms, prop-2-enyl or prop-2-ynyl;

$R^4$ and $R^5$ are the same or different and each is a benzyl or phenethyl group wherein the phenyl ring is optionally substituted by one or more of halogen, alkoxy having 1 to 3 carbon atoms and methylenedioxy;

A and B are the same or different and each is an alkylene radical containing 1,2 or 3 carbon atoms;

L is an alkylene chain having from 2 to 12 carbon atoms or is a group —$L^1.O.L^2$— wherein each of $L^1$ and $L^2$ is alkylene having at least two carbon atoms and taken together $L^1$ and $L^2$ have up to 11 carbon atoms; and $X^-$ is an anion.

Preferably A plus B have a total of at least 4 carbon atoms.

A preferred class of compounds of formula (I) are those represented by general formula (II):

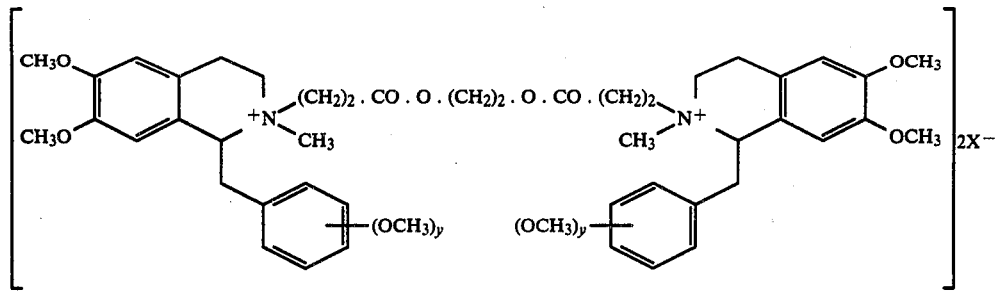

wherein
y is an integer 1,2 or 3, with the methoxy groups preferably in at least one of the 3-,4- and 5-positions;
n is an integer of from 2 to 8, preferably 4 to 7; and
$X^-$ is a pharmaceutically acceptable anion, for example a halide such as iodide, bromide, chloride, sulphate or an anion of an organic acid such as methanesulphonate, benzenesulphonate, nitrobenzenesulphonate and naphthalenesulphonate. Non-pharmaceutically acceptable salts of formula (I) are also included within the present invention as intermediates for conversion to pharmaceutically acceptable salts.

Valuable compounds of formula (II) include the compounds listed hereinbelow:
N,N'-dimethyl-N,N'-4,12-dioxa-3,13-dioxopentadecylene-1,15-bis-tetrahydropapaverinium salts,
(in II: n=7; (OMe)$_y$=3,4-dimethoxy);
N,N'-dimethyl-N,N'-4,9-dioxa-3,10-dioxododecylene-1,12-bis-tetrahydropapaverinium salts,
(in II: n=4; (OMe)$_y$=3,4-dimethoxy); and particularly preferred compounds are:
N,N'-dimethyl-N,N'-4,10-dioxa-3,11-dioxotridecylene-1,13-bis-tetrahydropapaverinium salts,
(in II: n=5, (OMe)$_y$=3,4-dimethoxy); and
N,N'-dimethyl-N,N'-4,11-dioxa-3,12-dioxotetradecylene-1,14-bis-tetrahydropapaverinium salts,
(in II: n=6, (OMe)$_y$=3,4-dimethoxy).

The compounds of formula (I) may be synthesised by any method known for making compounds of analogous structure, but preferably by quaternising the corresponding tertiary base of formula (III):

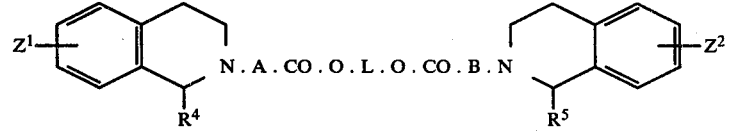

or a monoquaternary derivative thereof wherein one of the nitrogen atoms is quaternised by $R^2$ or $R^3$, as appropriate. In formula (III), $Z^1$, $Z^2$, $R^4$, $R^5$, A, B and L are as defined in formula (I). The quaternising agent may be designated as a reactive ester derivative of an alcohol $R^6OH$ wherein $R^6$ has the value of $R^2$ or $R^3$ as appropriate. If the base is being quaternised, then of course at least two molar equivalents of the quaternising ester are required, but it is preferably present in large excess. If a monoquaternary derivative of the base of formula (III) is being quaternised, then at least an equimolar quantity of the ester should be used.

The reaction may be performed in the absence of a solvent but preferably in a solvent such as an alkanol (eg. methanol), an aromatic hydrocarbon (eg. toluene), a chlorinated hydrocarbon (eg. chloroform), an aliphatic ketone (eg. acetone or methyl ethyl ketone), dioxan, tetrahydrofuran, dimethyl sulphoxide, acetonitrile or dimethyl formamide. Temperatures up to reflux may be used and the reaction optionally performed under pressure and optionally in the absence of light.

Suitable reactive ester derivatives include halide (eg. bromide or iodide), p-toluenesulphonate, methanesulphonate, benzenesulphonate, nitrobenzenesulphonate and naphthalenesulphonate esters. If the reactive ester derivative is denoted as $R^6Y$, Y is preferably chosen as a group which will provide the anion $X^-$ in the compound of formula (I), but if a different group is used as Y this may be changed to $X^-$ by simple metathesis methods such as double decomposition, on an ion exchange column or equivalent methods which are well known in the art.

The compounds of formula (I) may also be prepared from a compound of formula (IV):

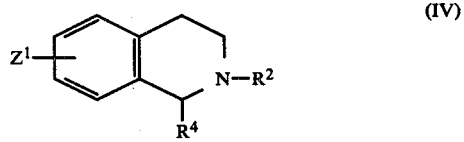

wherein $Z^1$, $R^2$ and $R^4$ have the same meaning as in formula (I) by reaction with a compound of formula (V):

wherein L has the same meaning as in formula (I), G and $G^1$ are the same or different and each is a group capable of reacting with a compound (IV) selected from a group —C($J^1$)=CH.$J^2$ and a reactive ester derivative of a group —J.OH, wherein J is alkylene having 1 to 3 carbon atoms, one of $J^1$ and $J^2$ is hydrogen and the other of $J^1$ and $J^2$ is hydrogen or methyl; and $G^1$ may also be selected from a group:

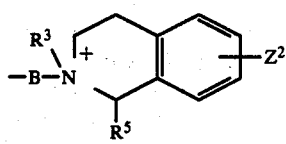

wherein B, $R^3$, $R^5$ and $Z^2$ each have the same meaning as in formula (I).

For the preparation of symmetrical compounds of formula (I), conveniently two molecules of a compound of formula (IV) are reacted with one molecule of formula (V) wherein G has the same meaning as $G^1$.

Suitable reactive ester derivatives of the group —J.OH include the halide (eg. chloride or bromide), methanesulphonate, p-toluenesulphonate, benzenesulphonate and sulphate esters.

Compounds of formula (I) may further be prepared by formation of the ester linkage in the central chain as the final synthetic step. For example, by reaction of a compound of formula (VI) with a compound of formula (VII):

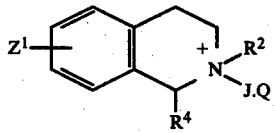

(VI):

$Q^1 . L . Q^2$   (VII)

wherein $Z^1$, $R^2$ and $R^4$ have the same meaning as in formula (I), L and J have the same meaning as in formula (V), Q and $Q^1$ are functional groups or atoms which react together to form an ester linkage, and $Q^2$ is a functional group or atom which will react with Q to form an ester linkage or is a group:

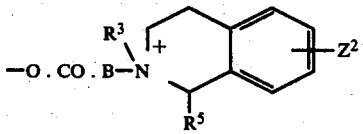

wherein B, $R^3$, $R^5$ and $Z^2$ have the same meaning as in formula (I).

Suitable groups for Q include carboxyl, the corresponding acid halide or acid anhydride, and carboxylate salt groups such as, for example, those with an alkali metal cation, or with an ammonium or silver cation; and $Q^1$ and $Q^2$ may be for example hydroxyl or halo. Where appropriate the reaction may conveniently be carried out in the presence of a catalyst such as an acid catalyst, or a condensing agent such as dicyclohexylcarbodiimide.

Alternatively, a compound of formula (VI) wherein Q is an ester group, for example methoxycarbonyl, may be transesterified with an alcohol of formula (VII) wherein $Q^1$ is hydroxyl, in the presence of an acid catalyst.

The intermediates of formula (III) may be conveniently synthesized by reacting a compound of formula (VIII) with a compound of formula (IX).

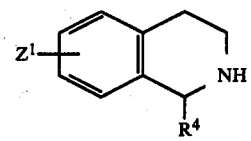

(VIII):

G . CO . O . L . O . CO . $G^2$   (IX):

wherein $Z^1$, $R^4$ and L have the same meaning as in formula (I), G and $G^2$ are the same or different and each is selected from a group —C($J^1$)=CH$J^2$ and a reactive ester derivative of the group —J.OH wherein J, $J^1$ and $J^2$ are as hereinbefore defined, and $G^2$ is also selected from a group:

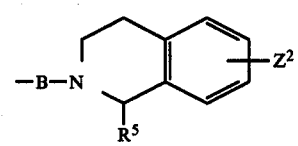

wherein B, $R^5$ and $Z^2$ have the same meaning as in formula (I).

In particular intermediates of formula (III) wherein at least one of A and B is —(CH$_2$)$_2$— optionally substituted by a methyl group are readily prepared by a Michael reaction between an acrylate ester of formula (IX) and a compound of formula (VIII), conveniently at an elevated temperature for example upto 100° C. or optionally in the presence of an inert liquid medium such as an aromatic hydrocarbon (eg benzene) at reflux temperature.

An intermediate of formula (V), (VII) or (IX) wherein $G^1$, $Q^2$ or $G^2$ respectively includes an isoquinolinium group may be prepared by reacting an appropriate compound of formula (IV), (VI) or (VIII) with an excess of a different compound of formula (V), (VII) or (IX) respectively wherein $G^1$, $Q^2$ or $G^2$ does not include an isoquinolinium group.

The compounds of formula (I) have 4 centres of asymmetry, one at each of the nitrogen atoms and the other at position 1 in each of the tetrahydroisoquinolinium rings.

The stereoisomerism of the compounds of formula (I) may be partly controlled by the use of a starting material of formula (VIII) of a defined stereochemical configuration, and thus provide a DD—, LL—, or meso base of formula (III). The quaternisation process however introduces the further 2 centres of asymmetry and usually results in the compounds of formula (I) being a mixture of stereoisomers. All stereoisomers of formula (I) are however within the scope of the present invention.

The compounds of formula (I) may be presented in a pharmaceutical formulation for intravenous administration. The formulation may be an aqueous solution which may contain bacteriostatic agents, antioxidants, buffers or other pharmaceutically acceptable additives. The compounds may also be administered by other parental routes as a solution, emulsion or suspension in a pharmaceutically acceptable liquid or mixture of liquids, which may contain bacteriostatic agents, antioxidants, buffers, thickening agents, suspending agents or other pharmaceutically acceptable additives. Such formulations are presented in unit dose forms such as ampoules or disposable injection devices, or in multi-dose forms such as a bottle from which the appropriate dose may be withdrawn. All such formulations should be rendered sterile. Alternatively the compounds may be presented as a dry powder with or without other excipients to be dissolved or suspended in a liquid medium prior to use.

A simple and preferred formulation is a solution of the compound of formula (I) in water. This may be prepared by simply dissolving the compound in previously sterilised pyrogen-free water under aseptic conditions and sterilising the solution.

The compounds of formula (I) may therefore be used to induce neuromuscular blockade in an animal including man. The dose to be used will vary according to the compound used and its stereoisomerism, and according to the rate of onset of paralysis the attendant physician wishes to induce. Suitable doses for intravenous injection are 0.1 to 4.0 mg per kg body weight of the subject, preferably 0.1 to 2.0 mg/kg, and conveniently 0.25 to 1.0 mg/kg. Hence a suitable unit dose of a compound of formula (I) comprises from 20 mg to 80 mg, and preferably from 40 mg to 60 mg; and a suitable injectable solution contains from 1 mg to 100 mg, preferably from 10 mg to 50 mg and most preferably from 20 to 30 mg of a compound of formula (I) per ml. Additional doses may be needed to maintain paralysis depending upon the length of surgical procedure. In view of the preferred mode of administration, preferred salts of formula (I) are those having a solubility of at least 20 mg/ml in water at room temperature.

The pharmacological properties of two of the compounds of formula (I) in comparison with those of the known compound gallamine are illustrated by the results shown in Table A. These show the mean intravenous doses required to produce 50% and 95% paralysis ($PD_{50}$ and $PD_{95}$ respectively) and 50% vagal blockade ($VD_{50}$) in 4 or 5 anaesthetised cats. The freedom of the compounds of the invention, Nos. 1c and 6c from inducing vagal blockade at paralysing doses is shown by the ratio $VD_{50}/PD_{95}$. All doses are mg. of compound per kg body weight.

TABLE A

| Compound | No. of cats | $PD_{50}$ | $PD_{95}$ | $VD_{50}$ | $VD_{50}/PD_{50}$ | $VD_{50}/PD_{95}$ |
|---|---|---|---|---|---|---|
| Gallamine | 4 | 0.85 | 1.8 | 0.56 | 0.66 | 0.31 |
| Compound 1c | 5 | 0.11 | 0.22 | 3.7 | 35 | 17 |
| Compound 6c | 4 | 0.092 | 0.16 | 2.7 | 31 | 17 |

It will be understood from the foregoing description and the examples set forth hereafter that what we will claim may comprise any novel feature herein, principally but not exclusively the following:

(a) a compound of formula (I), (II) and (III) as hereinbefore defined; and salts of a compound of formula (III) including a dioxalate salt;

(b) a method of preparing a compound of formula (I) wherein a tertiary amine of formula (III) containing at least six of the desired groupings in the desired diquaternary ammonium compound is reacted with a quaternising derivative of the remaining grouping, and if desired, the resulting salt is converted into the salt of another anion;

(c) a pharmaceutical formulation comprising a compound of formula (I) as the active ingredient together with a pharmaceutically acceptable carrier;

(d) a method of preparing a pharmaceutical formulation as defined under (c) which comprises the admixture of a compound of formula (I) with a pharmaceutically acceptable carrier therefor;

(e) a method of inducing neuromuscular paralysis in a mammal including man comprising the administration to the mammal of an effective neuromuscular paralysing amount of a compound of formula (I).

(f) a compound of formula (II) wherein n is 4,5,6 or 7;

(g) a compound of formula (II) wherein y is 2 and the methoxy groups are in the 3- and 4-positions;

(h) a compound of formula (I) wherein $Z^1$ and $Z^2$ each represent two methoxy substituents on adjacent carbon atoms;

(i) a compound of formula (I) wherein $Z^1$ and $Z^2$ each represent two methoxy substituents in the 6- and 7-positions; and (j) a compound of formula (I) wherein $Z^1$, $R^2$ and $R^4$ each have the same value as $Z^2$, $R^3$ and $R^5$ respectively.

The following are examples of the invention. In these examples:

All temperatures are in degrees Celsius.
"m.p." means melting point.
"b.p." means boiling point.
"mm Hg" means millimeters of mercury.
"Tlc" means thin layer chromatography.
"$P_2O_5$" means phosphorus pentoxide.
"mesylate" means methanesulphonate.
"besylate" means benzenesulphonate.
"tosylate" means toluenesulphonate.
"naphsylate" means naphthalenesulphonate.

EXAMPLE A

Injectable Preparation

1. Compound 1d, (2.5 g), is dissolved in 100 ml water for injection B.P. and the resulting solution sterilised by filtration through a membrane filter of 0.22 μm pore size. The sterilised solution is filled into 2 ml ampoules which are sealed aseptically. Each ampoule provides a dose of 50 mg of salt.

2. A solution of Compound 1d is made up as before, sterilised by filtration, filled into ampoules (2 ml per ampoule), freeze dried, and the ampoules sealed aseptically.

Immediately before use, the ampoules are opened and the compound redissolved in 2 ml water for injection B.P. to provide an injectable solution containing a dose of 50 mg of salt.

EXAMPLE B

Solution for Injection

| | |
|---|---|
| Compound 1d | 2.5 g |
| Chlorocresol | 10 mg |
| $NaH_2PO_4$ | 20 mg |
| Water for Injection B.P. | to 100 ml |

A solution is made up comprising the above ingredients and then brought to pH 4 using dilute phosphoric acid, sterilised by filtration and filled into a sterilised container which is aseptically sealed with a rubber stopper.

Desired doses may be withdrawn as required through the stopper.

EXAMPLE 1

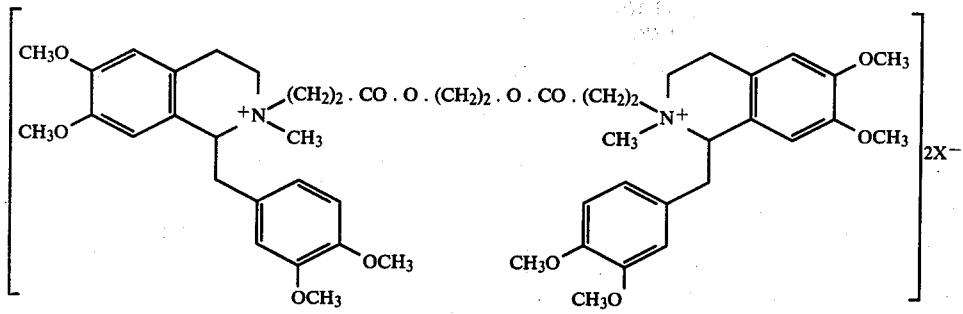

Acryloyl chloride (0.2 mole) in dry benzene (60 ml) was added over 0.5 hr with mechanical stirring to pentane-1,5-diol (0.1 mole), triethylamine (0.2 mole) and pyrogallol (0.1 g) in dry benzene (100 ml). Further dry benzene (ca 100 ml) was added followed by triethylamine (10 ml), and the mixture stirred at 50° C. for 0.5 hr. The triethylamine hydrochloride was filtered off and the solvent removed in vacuo to leave a yellow oil which was distilled in the presence of a trace of p-methoxyphenol, excluding light, to give 1,5-pentamethylene diacrylate (12.9 g; 61%; b.p. 90°–95° C./0.01 mmHg).

A solution of tetrahydropapaverine (4.43 g) and 1,5-pentamethylene diacrylate (1.30 g) in dry benzene (15 ml) was stirred under reflux for 48 hrs. excluding light. The solvent was removed in vacuo and the residual pale red oil dissolved in chloroform (10 ml). Addition of ether (ca 400 ml), followed by saturated ethereal oxalic acid solution (ca 500 ml) gave a flocculent white precipitate, which was filtered off, washed with ether and dried. Crystallisation (twice) from ethanol gave N,N'-4,10-dioxa-3,11-dioxotridecylene-1,13-bis-tetrahydropapaverine dioxalate as a white powder (3.5 g; 51%; m.p. 117°–121° C.).

The free base, N,N'-4,10-dioxa-3,11-dioxotridecylene-1,13-bis-tetrahydropapaverine, (Compound 1a), was obtained by basifying an aqueous solution of the dioxalate with sodium bicarbonate solution, followed by extraction with toluene and evaporation of the solvent, to give a colourless viscous oil.

Scrupulously dried base (0.5 g) in spectroscopically pure acetonitrile (8 ml) was treated with methyl iodide (8 ml) at room temperature for 22 hrs. The filtered reaction mixture was added dropwise to methanically stirred, filtered, dry ether (ca 450 ml). The flocculent white precipitate was filtered off, washed with dry ether, and dried in vacuo over $P_2O_5$ at 50° C. to yield N,N'-dimethyl-N,N'-4,10-dioxa-3,11-dioxotridecylene-1,13-bis-tetrahydropapaverinium di-iodide (Compound 1b: m.p. 143°–148° C. with softening at 138° C.).

Using the same technique as above, but replacing the methyl iodide by methyl methanesulphonate, methyl benzenesulphonate, methyl toluenesulphonate, methyl naphthalene-1-sulphonate and methyl naphthalene-2-sulphonate, and using a reaction time of 48 hrs. instead of 22 hrs., the following salts were prepared:

(1c) N,N'-dimethyl-N,N'-4,10-dioxa-3,11-dioxotridecylene-1,13-bis-tetrahydropapaverinium dimesylate, a white powder m.p. 104°–112° C.;

(1d) N,N'-dimethyl-N,N'-4,10-dioxa-3,11-dioxotridecylene-1,13-bis-tetrahydropapaverinium dibesylate, an off-white powder m.p. 85°–90° C., softening from 60° C.;

(1e) N,N'-dimethyl-N,N'-4,10-dioxa-3,11-dioxotridecylene-1,13-bis-tetrahydropapaverinium ditosylate, a white powder m.p. 70°–90° C.;

(1f) N,N'-dimethyl-N,N'-4,10-dioxa-3,11-dioxotridecylene-1,13-bis-tetrahydropapaverinium dinaph-1-sylate, a pale yellow powder m.p. 65°–85° C.; and (1g) N,N'-dimethyl-N,N'-4,10-dioxa-3,11-dioxotridecylene-1,13-bis-tetrahydropapaverinium dinaph-2-sylate, a white powder m.p. 60°–80° C.

EXAMPLES 2 TO 10

By methods analogous to that described in Example 1 were synthesised, via the corresponding oxalate salts, the following tertiary bases (2a to 15a):

(2a) N,N'-4,10-dioxa-3,11-dioxotridecylene-1,13-bis-D-(−)-tetrahydropapaverine, a colourless viscous oil, $[\alpha]_D^{23.5} -53.62°$ (c, 1.408 in chloroform);

(3a) N,N'-4,10-dioxa-3,11-dioxotridecylene-1,13-bis-L-(+)-tetrahydropapaverine, a colourless viscous oil, $[\alpha]_D^{23} +62.65°$ (c, 0.961 in chloroform);

(4a) N,N'-7-methyl-4,10-dioxa-3,11-dioxotridecylene-1,13-bis-tetrahydropapaverine;

(5a) N,N'-4,10-dioxa-3,11-dioxotridecylene-1,13-bis-1',2',3',4'-tetrahydro-6',7'-dimethoxy-1-{2''-(3'',4''-dimethoxyphenyl)ethyl}isoquinoline, a colourless viscous oil;

(6a) N,N'-4,11-dioxa-3,12-dioxotetradecylene-1,14-bis-tetrahydropapaverine;

(7a) N,N'-4,9-dioxa-3,10-dioxododecylene-1,12-bis-(±)-tetrahydropapaverine, a colourless solid, m.p. 44°–46° C.;

(8a) N,N'-4,9-dioxa-3,10-dioxododecylene-1,12-bis-D-(−)-tetrahydropapaverine, a colourless solid, m.p. 47°–49° C., $[\alpha]_D^{20} -70.6°$ (c, 0.395 in chloroform);

(9a) N,N'-4,9-dioxa-3,10-dioxododecylene-1,12-bis-L-(+)-tetrahydropapaverine, a colourless solid m.p. 48.50° C. $[\alpha]_D^{20} +71.2$ (c, 1.215 in chloroform);

(10a) N,N'-4,8-dioxa-3,9-dioxoundecylene-1,11-bis-tetrahydropapaverine, a colourless solid, m.p. 46°–48° C.;

(11a) N,N'-4,7-dioxa-3,8-dioxodecylene-1,10-bis[1',2',3',4'-tetrahydro-6',7'-dimethoxy-1-(3'',4'',5''-trimethoxybenzyl)isoquinoline], a colourless solid m.p. 46°–47° C.;

(12a) N,N'-4,7-dioxa-3,8-dioxodecylene-1,10-bis[1',2',3',4'-tetrahydro-6',7'-dimethoxy-1-(2''-bromo-4'',5''-dimethoxybenzyl)isoquinoline], a colourless solid m.p. 65°–67° C.;

(13a) N,N'-4,7-dioxa-3,8-dioxodecylene-1,10-bis[1',2',3',4'-tetrahydro-6',7'-dimethoxy-1-(3'',4''- methylenedioxybenzyl)isoquinoline], a colourless solid m.p. 44°–46° C.;

(14a) N,N'-4,7-dioxa-3,8-dioxodecylene-1,10-bis[1',2',3',4'-tetrahydro-6',7'-dimethoxy-1-(3",4"-dichlorobenzyl)isoquinoline], a colourless solid m.p. 45°–48° C.; and (15a) N,N'-4,7-dioxa-3,8-dioxodecylene-1,10-bis[1',2',3',4'-tetrahydro-6',7'-dimethoxy-1-(2",5"-dimethoxybenzyl)isoquinoline], a colourless solid m.p. 44°–46° C.; from which were prepared the corresponding salts of formula (I), 2b to 15b:

(2b) N,N'-dimethyl-N,N'-4,10-dioxa-3,11-dioxotridecylene-1,13-bis-D-(−)-tetrahydropapaverinium dimesylate, m.p. 110°–114° C. with softening at 95°–97° C., $[\alpha]_D^{24.5}$ −41.67° (c, 1.323 in chloroform);

(3b) N,N'-dimethyl-N,N'-4,10-dioxa-3,11-dioxotridecylene-1,13-bis-L-(+)-tetrahydropapaverinium dimesylate, m.p. 110°–114° C. with softening at 95°–97° C., $[\alpha]_D^{24}$ +40.26 (c, 1.016 in chloroform);

(4b) N,N'-dimethyl-N,N'-7-methyl-4,10-dioxa-3,11-dioxotridecylene-1,13-bis-tetrahydropapaverinium dimesylate, a white powder, m.p. 100.5°–109° C.;

(5b) N,N'-dimethyl-N,N'-4,10-dioxa-3,11-dioxotridecylene-1,13-bis-{1',2',3',4'-tetrahydro-6',7'-dimethoxy-1-[2-(3",4"-dimethoxyphenyl)ethyl]isoquinolinium} dimesylate, m.p. 98°–105° C.;

(6b) N,N'-dimethyl-N,N'-4,11-dioxa-3,12-dioxatetradecylene-1,14-bis-tetrahydropapaverinium di-iodide, m.p. 132°–138° C.;

(6c) N,N'-dimethyl-N,N'-4,11-dioxa-3,12-dioxotetradecylene-1,14-bis-tetrahydropapaverinium dimesylate, a white powder, m.p. 109°–118° C.;

(7b) N,N'-dimethyl-N,N'-4,9-dioxa-3,10-dioxododecylene-1,12-bis-(+)-tetrahydropapaverinium dimesylate, m.p. 91°–115° C.; (8b) N,N'-dimethyl-N,N'-4,9-dioxa-3,10-dioxododecylene-1,12-bis-D-(−)-tetrahydropapaverinium dimesylate, m.p. 105°–115° C., $[\alpha]_D^{18}$ −51.18° (c, 1.105 in chloroform);

(9b) N,N'-dimethyl-N,N'-4,9-dioxa-3,10-dioxododecylene-1,12-bis-L-(+)-tetrahydropapaverinium dimesylate, m.p. 102°–113° C., $[\alpha]_D^{18}$ +50.28° (c, 1.093 in chloroform);

(10b) N,N'-dimethyl-N,N'-4,8-dioxa-3,9-dioxoundecylene-1,11-bis-tetrahydropapaverinium dimesylate, a white solid m.p. 96°–120° C.;

(11b) N,N'-dimethyl-N,N'-4,7-dioxa-3,8-dioxodecylene-1,10-bis[1',2',3',4'-tetrahydro-6',7'-dimethoxy-1-(3",4",5"-trimethoxybenzyl)isoquinolinium]-dimesylate, m.p. 123°–138° C.;

(12b) N,N'-dimethyl-N,N'-4,7-dioxa-3,8-dioxodecylene-1,10-bis[1',2',3',4'-tetrahydro-6',7'-dimethoxy-1-(2-bromo-4",5"-dimethoxybenzyl)isoquinolinium]dimesylate, m.p. 128°–140° C.;

(13b) N,N'-dimethyl-N,N'-4,7-dioxa-3,8-dioxodecylene-1,10-bis[1',2',3',4'-tetrahydro-6',7'-dimethoxy-1-(3",4"-methylenedioxybenzyl)isoquinolinium]-dimesylate, m.p. 121°–132° C.;

(14b) N,N'-dimethyl-N,N'-4,7-dioxa-3,8-dioxodecylene-1,10-bis[1',2',3',4'-tetrahydro-6',7'-dimethoxy-1-(3",4"-dichlorobenzyl)isoquinolinium]dimesylate, m.p. 111°–120° C.; and (15b) N,N'-dimethyl-N,N'-4,7-dioxa-3,8-dioxodecylene-1,10-bis[1',2',3',4'-tetrahydro-6',7'-dimethoxy-1-(2",5"-dimethoxybenzyl isoquinolinium]dimesylate, m.p. 86°–95° C.

EXAMPLE 16

N,N'-4,12-Dioxa-3,13-dioxopentadecylene-1,15-bis-tetrahydropapaverine (Compound 16a), a viscous oil, was prepared by the method described in Example 1.

This scrupulously dried compound (0.5 g) in chloroform (10 ml) was treated with methyl iodide (10 ml) at room temperature for 22 hrs. The filtered reaction mixture was added dropwise to mechanically stirred, filtered, dry ether (ca 450 ml). The flucculent white precipitate was filtered off, washed with dry ether and dried in vacuo over $P_2O_5$ at 50° C. to yield N,N'-dimethyl-N,N'-4,12-dioxa-3,13-dioxopentadecylene-1,15-bis-tetrahydropapaverinium di-iodide, m.p. 114°–123° C. (Compound 16b).

EXAMPLES 17 TO 23

Using the method described in Example 16 were prepared Compounds 17a to 23a:

(17a) N,N'-4,13-dioxa-3,14-dioxohexadecylene-1,16-bis-tetrahydropapaverine, a viscous oil.

(18a) N,N'-4,7-dioxa-3,8-dioxodecylene-1,10-bis-(±)-tetrahydropapaverine, a colourless solid m.p. 47°–49° C.;

(19a) N,N'-4,7-dioxa-3,8-dioxodecylene-1,10-bis-[1',2',3',4'-tetrahydro-1'-(3",4"-dimethoxybenzyl)-6',7'-methylenedioxyisoquinoline], a colourless solid m.p. 49°–50° C.;

(20a) N,N'-4,10-dioxa-3,11-dioxotridecylene-1,13-bis[1',2',3',4'-tetrahydro-1'-(3",4"-dimethoxybenzyl)6',7'-methylenedioxyisoquinoline] a colourless viscous oil;

(21a) N,N'-4,7-dioxa-3,8-dioxodecylene-1,10-bis[1',2',3',4'-tetrahydro-6',7'-dimethoxy-1'-benzylisoquinoline], a colourless oil;

(22a) N,N'-4,7-dioxa-3,8-dioxodecylene-1,10-bis[1',2',3',4'-tetrahydro-6',7'-dimethoxy-1'-(4"-methoxybenzyl)isoquinoline], a colourless viscous oil;

(23a) N,N'-4,7,10-trioxa-3,11-dioxotridecylene-1,13-bis-tetrahydropapaverine, a colourless semi-solid; and the corresponding salts of formula (I):

(17b) N,N'-dimethyl-N,N'-4,13-dioxa-3,14-dioxohexadecylene-1,16-bis-tetrahydropapaverinium di-iodide, m.p. 119°–123° C.;

(18b) N,N'-dimethyl-N,N'-4,7-dioxa-3,8-dioxodecylene-1,10-bis-(±)-tetrahydropapaverinium di-iodide, m.p. 120°–130° C.;

(18c) N,N'-dimethyl-N,N'-4,7-dioxa-3,8-dioxodecylene-1,10-bis-(±)-tetrahydropapaverinium dimesylate, m.p. 99°–108° C. (made by the method of Example 1);

(19b) N,N'-dimethyl-N,N'-4,7-dioxa-3,8-dioxodecylene-1,10-bis-[1',2',3',4'-tetrahydro-1'-(3",4"-dimethoxybenzyl)-6',7'-methylenedioxyisoquinolinium]di-iodide, m.p. 144°–148° C.;

(20b) N,N'-dimethyl-N,N'-4,10-dioxa-3,11-dioxotridecylene-1,13-bis[1',2',3',4'-tetrahydro-1'-(3",4"-dimethoxybenzyl)-6',7'-methylenedioxyisoquinolinium]di-iodide, m.p. 122°–129° C.;

(21b) N,N'-dimethyl-N,N'-dioxa-3,8-dioxodecylene-1,10-bis(1',2',3',4'-tetrahydro-6',7'-dimethoxy-1'-benzylisoquinolinium)di-iodide, m.p. 141°–145° C.;

(22b) N,N'-dimethyl-N,N'-4,7-dioxa-3,8-dioxodecylene-1,10-bis[1',2',3',4'-tetrahydro-6',7'-dimethoxy-1'-(4"-methoxybenzyl)isoquinolinium]di-iodide, m.p. 143°–150° C.; and (23b) N,N'-dimethyl-N,N'-4,7,10-trioxa-3,11-dioxotridecylene-1,13-bis-tetrahydropapaverinium di-iodide, m.p. 119°–128° C.

EXAMPLE 24

The base (Compound 24a), N,N'-4,7-dioxa-3,8-dioxodecylene-1,10-bis-D-(−)-tetrahydropapaverine, a colourless solid m.p. 47°–49° C., $[\alpha]_D^{21.5}-58.2°$ (c, 1.323 in chloroform) and corresponding N,N'-dimethyl-N,N'-4,7-dioxa-3,8-dioxodecylene-1,10-bis-D-(−)-tetrahydropapaverinium dimesylate, m.p. 105°–113° C., $[\alpha]_D^{21.5}-55.9°$ (c, 0.948 in chloroform), designated Compound 24b, were prepared by the method of Example 1.

Further base (0.58 g) and redistilled methyl iodide (5 ml) were refluxed in dry benzene (10 ml) for 6 hrs. The precipitated solid was dissolved in methanol, and the solution added dropwise to mechanically stirred, filtered, dry ether (500 ml). The flucculent white solid was filtered off, washed with dry ether and dried in vacuo over $P_2O_5$ to yield N,N'-dimethyl-N,N'-4,7-dioxa-3,8-dioxodecylene-1,10-bis-D-(−)-tetrahydropapaverinium di-iodide, m.p. 122°–125° C., $[\alpha]_D^{20}-48.9°$ (c, 1.208 in chloroform) designated Compound 24c.

EXAMPLE 25

Using the procedures described in Example 24 were prepared:
(25a) N,N'-4,7-dioxa-3,8-dioxodecylene-1,10-bis-L-(+)-tetrahydropapaverine, a colourless solid, m.p. 48°–50° C., $[\alpha]_D^{21.5}+58.9°$ (c, 1.021 in chloroform);
(25b) N,N'-dimethyl-N,N'-4,7-dioxa-3,8-dioxodecylene-1,10-bis-L-(+)-tetrahydropapaverinium dimesylate, m.p. 105°–114° C., $[\alpha]_D^{21.5}+56.4°$ (c, 1.140 in chloroform); and
(25c) N,N'-dimethyl-N,N'-4,7-dioxa-3,8-dioxodecylene-1,10-bis-L-(+)-tetrahydropapaverinium di-iodide, m.p. 122°–126° C., $[\alpha]_D^{20}+48.1°$ (c, 1.105 in chloroform).

EXAMPLE 26

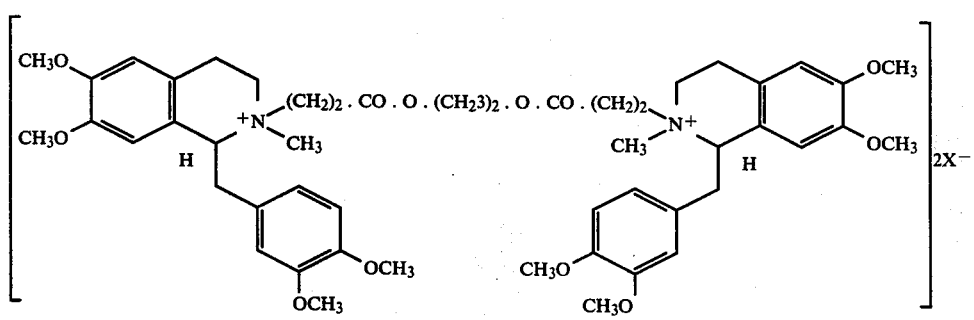

D-(+)-Tetrahydropapaverine (2.07 g) in dry benzene was added dropwise to 1,5-pentamethylene diacrylate (7.66 g) in dry benzene, and the mixture refluxed for 4 hrs. The solvent was evaporated in vacuo, and the oily residue washed three times with light petroleum (b.p. 40°–60° C.). The oily residue was dissolved in benzene and light petroleum added to precipitate the oil. Resolution in benzene and re-precipitation with light petroleum twice more gave a brown oily mass of D-(−)-1-tetrahydropapaverin-2'-yl-4,10-dioxa-3,11-dioxotridec-12-ene, $[\alpha]_D^{25.5}-41.17°$ (c, 1.388 in chloroform). TLC Polygram Sil G/UV $_{254}$ in ethanol-ethylacetate (1:1), single spot $R_f 0.56$ $\nu_{max}$: 1740 cm$^{-1}$ (ester C=O) and 1650 cm$^{-1}$ (>C=CH$_2$).

D-(−)-1-Tetrahydropapaverin-2'-yl-4,10-dioxa-3,11-dioxotridec-12-ene (1.38 g) and L-(−)-tetrahydropapaverine (0.847 g) were refluxed in dry benzene for 48 hours with constant stirring. The solvent was evaporated, the residue dissolved in chloroform, and the solution treated with a saturated solution of oxalic acid in dry ether. The precipitate was recrystallised from ethanol to yield meso-N,N'-4,10-dioxa-3,11-dioxotridecylene-1,13-bis-tetrahydropapaverine dioxalate, a colourless solid m.p. 103°–107° C., $[\alpha]_D^{23} \pm 0°$ (c, 1.183 in water).

By the method described in Example 1 was obtained the free base meso-N,N'-4,10-dioxa-3,11-dioxotridecylene-1,13-bis-tetrahydropapaverine, a colourless viscous oil $[\alpha]_D^{22.5}\pm 0°$ (c, 1.018 in chloroform), and thence meso—N,N'-dimethyl-N,N'-4,10-dioxa-3,11-dioxotridecylene-1,13-bis-tetrahydropapaverinium dimesylate, m.p. 102°–107° C. with softening at 97°–99° C., $[\alpha]_D^{20}\pm 0°$ (c, 0.935 in chloroform). The base and salt are designated Compounds (26a) and (26b) respectively.

EXAMPLE 27

The following compounds were prepared using the method described in Example 26:
(27a) meso-N,N'-4,7-dioxa-3,8-dioxodecylene-1,10-bis-tetrahydropapaverine, a gummy solid; and
(27b) meso-N,N'-dimethyl-N,N'-4,7-dioxa-3,8-dioxodecylene-1,10-bis-tetrahydropapaverinium dimesylate, m.p. 100°–112° C., $[\alpha]_D^{21}\pm 0°$ (c, 0.409 in chloroform).

EXAMPLE 28

A γ-butyrolactone (36 g) and propane-1,3-diol (15.2 g) mixture at 0.5° C. was saturated over 2 hrs. with hydrogen bromide gas and then left at 0° C. for 24 hrs. The mixture was added to water (300 ml) and extracted with ethylene dibromide (2×100 ml). The combined extracts were washed with water, dried (Na$_2$SO$_4$) and evaporated to leave an oil. The major distillable component (ca 50 g; b.p. 106°–140° C./0.05 mmHg) was 3-bromo-1-propyl 4-bromobutanoate. The viscous pot residue was extracted with petroleum ether (60°–80° C.; 3×150 ml) and the combined extracts evaporated to leave a colourless oil shown by i.r. and n.m.r. data to be propane-1,3-bis-(4-bromobutanoate).

Propane-1,3-bis(4-bromobutanoate) (1.8 g) in refluxing dry toluene (10 ml) was treated with tetrahydropapaverine (6.8 g) in toluene (50 ml) dropwise over 0.5 hr. The mixture was refluxed for 18 hrs., cooled and filtered from tetrahydropapaverine hydrobromide. The filtrate was evaporated in vacuo and the residual oil dissolved in chloroform (10 ml). Addition of ether (ca 500 ml), followed by saturated ethereal oxalic acid solution (ca 500 ml) gave a flocculent white precipitate which was filtered off, washed with ether and dried. Crystallisation from ethanol (twice) gave N,N'-5,9-dioxa-4,10-dioxotridecylene-1,13-bis-tetrahydropapaverine dioxalate as a white powder, m.p. 107°–115° C.

By methods described in Example 1 were obtained the corresponding base N,N'-5,9-dioxa-4,10-dioxotridecylene-1,13-bis-tetrahydropapaverine, a colourless viscous oil, and N,N'-dimethyl-N,N'-5,9-dioxa-4,10-dioxotridecylene-1,13-bis-tetrahydropapaverinium dimesylate, a white solid m.p. 95°–102° C., which are designated Compounds (28a) and (28b) respectively.

EXAMPLE 29

1,2,3,4-Tetrahydro-2-(2-methoxycarbonylethyl)-2'-methylpapaverinium benzenesulphonate (0.8 g) was treated with a solution of pentamethylene glycol (67.5 mg) and benzenesulphonic acid (30 mg) in methylene chloride (5 ml). After evaporation of solvents the residue was heated on the steam bath under reduced pressure (ca 150 mmHg) for 24 hrs. Finally the gummy product was dissolved in acetone (25 ml) and slowly added to well-stirred ether (250 ml). The product was a white, somewhat deliquescent powder, and found to have a thin layer chromatogram consistent with the presence of Compound (1d).

EXAMPLE 30

3-Methylpentane-1,5-diol, the substance used in the synthesis of Compound 4a, was prepared as follows:

Lithium aluminium hydride (20 g) in dry ether (150 ml) at 0.5° C. was treated dropwise with 3-methylglutaric anhydride (25 g) in a dry ethertetrahydrofuran mixture (1:1, 200 ml), with stirring, over 0.5 hr. The mixture was refluxed for 6 hrs. cooled to 0.5° C. and the complex and excess hydride destroyed by careful addition of water (25 ml), sodium hydroxide solution (5 N; 18.5 ml) and then water (87.5 ml). The inorganic salts were filtered off, the solvents removed in vacuo and the oil distilled to give 3-methylpentane-1,5-diol (b.p. 110°–112.5° C./0.7 mmHg).

Further characterising data of the compounds hereinbefore identified is provided in the following Tables. Compounds identified by a number alone represent the oxalate salt of the corresponding base identified by the number and letter 'a'; for example, Compound (1) is N,N'-4,10-dioxa-3,11-dioxotridecylene-1,13-bis-tetrahydropapaverinedioxalate.

Table 1: Elemental Analysis
Table 2: Infra-Red spectra
Table 3: Nuclear Magnetic Resonance spectra and Rf value obtained using t.l.c. (Polygram Sil G/UV$_{254}$ in ethanol-ethyl acetate (1:1) with iodoplatinate spray visualisation).

TABLE 1

| Compound No. | Empirical Formula | (Analysis) Calculated % | | | Found % | | |
|---|---|---|---|---|---|---|---|
| | | C | H | N | C | H | N |
| 1 | $C_{55}H_{70}N_2O_{20}$ | 61.22 | 6.49 | 2.60 | 61.13 | 6.27 | 2.49 |
| 1b | $C_{53}H_{72}I_2N_2O_{12}$ | 53.80 | 6.09 | 2.37 | 53.87 | 6.18 | 2.12 |
| 1c | $C_{55}H_{78}N_2O_{18}S_2 \cdot 2H_2O$ | 57.8 | 7.10 | 2.43 | 57.03 | 6.80 | 2.56 |
| 1d | $C_{65}H_{82}N_2O_{18}S_2 \cdot H_2O$ | 61.9 | 6.7 | 2.2 | 62.35 | 6.73 | 2.20 |
| 1e | $C_{67}H_{86}N_2O_{18}S_2 \cdot 2H_2O$ | 61.7 | 6.95 | 2.14 | 61.76 | 7.04 | 2.06 |
| 1f | $C_{73}H_{86}N_2O_{18}S_2 \cdot 3H_2O$ | 62.75 | 6.6 | 2.0 | 63.29 | 6.21 | 1.77 |
| 1g | $C_{73}H_{86}N_2O_{18}S_2 \cdot 2H_2O$ | 63.55 | 6.55 | 2.03 | 63.31 | 6.44 | 1.95 |
| 2 | $C_{55}H_{70}N_2O_{20} \cdot 2H_2O$ | 59.24 | 6.64 | 2.51 | 59.05 | 6.31 | 2.69 |
| 2b | $C_{55}H_{78}N_2O_{18} \cdot 2H_2O$ | 57.19 | 7.11 | 2.43 | 57.34 | 6.88 | 2.18 |
| 3 | $C_{55}H_{70}N_2O_{20} \cdot 2H_2O$ | 59.24 | 6.64 | 2.51 | 59.08 | 6.35 | 2.32 |
| 3b | $C_{55}H_{78}N_2O_{18}S_2 \cdot 2H_2O$ | 57.19 | 7.11 | 2.43 | 57.44 | 6.90 | 2.40 |
| 4b | $C_{56}H_{80}N_2O_{18}S_2 \cdot 2H_2O$ | 58.43 | 7.13 | 2.43 | 58.03 | 7.37 | 2.17 |
| 5b | $C_{57}H_{82}N_2O_{18}S_2 \cdot 3H_2O$ | 57.00 | 7.33 | 2.33 | 57.12 | 7.10 | 2.12 |
| 6b | $C_{54}H_{74}I_2N_2O_{12} \cdot 2H_2O$ | 52.60 | 6.33 | 2.77 | 52.53 | 6.44 | 2.20 |
| 6c | $C_{56}H_{80}N_2O_{18}S_2 \cdot 1H_2O$ | 58.43 | 7.13 | 2.43 | 58.07 | 6.87 | 2.25 |
| 7b | $C_{54}H_{76}N_2O_{18}S_2 \cdot 4H_2O$ | 55.1 | 7.1 | 2.38 | 55.41 | 6.61 | 2.38 |
| 8 | $C_{54}H_{68}N_2O_{20} \cdot H_2O$ | 59.88 | 6.47 | 2.59 | 60.28 | 6.35 | 2.45 |
| 8b | $C_{54}H_{76}N_2O_{18}S_2 \cdot 2H_2O$ | 56.84 | 7.02 | 2.46 | 56.68 | 6.79 | 2.34 |
| 9 | $C_{54}H_{68}N_2O_{20} \cdot H_2O$ | 59.88 | 6.47 | 2.59 | 59.88 | 6.34 | 2.48 |
| 9b | $C_{54}H_{76}N_2O_{18}S_2 \cdot 2H_2O$ | 56.81 | 7.02 | 2.46 | 56.43 | 6.88 | 2.33 |
| 10b | $C_{53}H_{74}N_2O_{18}S_2 \cdot H_2O$ | 57.40 | 6.86 | 2.53 | 57.41 | 6.68 | 2.54 |
| 11b | $C_{54}H_{76}N_2O_{20}S_2 \cdot 1.5H_2O$ | 55.72 | 6.80 | 2.40 | 55.80 | 7.03 | 2.32 |
| 12b | $C_{52}H_{70}Br_2N_2O_{18}S_2 \cdot 2H_2O$ | 49.13 | 5.83 | 2.20 | 49.04 | 5.76 | 2.15 |
| 13b | $C_{50}H_{64}N_2O_{18}S_2 \cdot 1.5H_2O$ | 56.02 | 6.26 | 2.6 | 56.05 | 6.58 | 2.59 |
| 14b | $C_{48}H_{60}Cl_2N_2O_{14}S_2 \cdot O \cdot 5H_2O$ | 52.22 | 5.53 | 2.54 | 52.33 | 5.57 | 2.61 |
| 15b | $C_{52}H_{72}N_2O_{18}S_2 \cdot 2.5H_2O$ | 55.66 | 6.86 | 2.50 | 55.74 | 7.23 | 2.40 |
| 16b | $C_{55}H_{76}I_2N_2O_{12}$ | 54.54 | 6.28 | 2.29 | 53.07 | 6.46 | 2.29 |
| 17b | $C_{56}H_{78}I_2N_2O_{12}$ | 54.90 | 6.37 | 2.29 | 55.39 | 6.49 | 2.25 |
| 18 | $C_{52}H_{64}N_2O_{20} \cdot 2H_2O$ | 58.21 | 6.34 | 2.61 | 58.29 | 5.98 | 2.58 |
| 18b | $C_{50}H_{66}I_2N_2O_{12}$ | 52.63 | 5.98 | 2.45 | 52.41 | 6.04 | 2.6 |
| 18c | $C_{52}H_{72}N_2O_{18}S_2 \cdot 3H_2O$ | 55.22 | 6.90 | 2.48 | 55.00 | 6.59 | 2.26 |
| 19b | $C_{48}H_{58}I_2N_2O_{12}$ | 51.99 | 5.27 | 2.53 | 51.72 | 5.25 | 2.25 |
| 20b | $C_{51}H_{64}I_2N_2O_{12}$ | 53.22 | 5.57 | 2.43 | 53.54 | 5.49 | 2.20 |
| 21b | $C_{46}H_{58}I_2N_2O_8 \cdot H_2O$ | 53.18 | 5.78 | 2.70 | 53.62 | 5.74 | 2.48 |
| 22b | $C_{48}H_{62}I_2N_2O_{10} \cdot H_2O$ | 52.46 | 5.83 | 2.55 | 52.38 | 5.73 | 2.37 |
| 23b | $C_{52}H_{70}I_2N_2O_{13}$ | 52.70 | 5.91 | 2.38 | 52.99 | 6.1 | 2.36 |
| 24 | $C_{52}H_{64}N_2O_2 \cdot H_2O$ | 59.2 | 6.26 | 2.66 | 58.9 | 6.27 | 2.86 |
| 24b | $C_{52}H_{72}N_2O_{18}S_2 \cdot 3H_2O$ | 55.22 | 6.9 | 2.48 | 54.8 | 6.55 | 2.36 |
| 24c | $C_{50}H_{66}N_2I_2$ | 52.63 | 5.79 | 2.45 | 52.37 | 6.12 | 2.32 |
| 25 | $C_{52}H_{64}N_2O_2 \cdot H_2O$ | 59.2 | 6.26 | 2.66 | 58.9 | 6.27 | 2.86 |
| 25b | $C_{52}H_{72}N_2O_{18}S_2 \cdot 3H_2O$ | 55.22 | 6.9 | 2.48 | 55.56 | 6.58 | 2.32 |
| 25c | $C_{50}H_{66}I_2N_2O_{12}$ | 52.6 | 5.79 | 2.45 | 52.46 | 6.04 | 2.28 |
| 26 | $C_{55}H_{70}N_2O_2 \cdot H_2O$ | 60.22 | 6.57 | 2.55 | 60.54 | 6.52 | 2.54 |

TABLE 1-continued

| Compound No. | Empirical Formula | (Analysis) Calculated % | | | Found % | | |
|---|---|---|---|---|---|---|---|
| | | C | H | N | C | H | N |
| 26b | $C_{55}H_{78}N_2O_8S_2 \cdot 2H_2O$ | 57.19 | 7.11 | 2.43 | 57.06 | 7.54 | 2.47 |
| 27 | $C_{52}H_{64}N_2O_{20} \cdot H_2O$ | 59.20 | 6.26 | 2.66 | 59.67 | 6.01 | 2.84 |
| 27b | $C_{52}H_{72}N_2O_{18}S_2 \cdot 3H_2O$ | 55.22 | 6.9 | 2.48 | 55.43 | 6.72 | 2.37 |
| 28b | $C_{55}H_{78}N_2O_{18}S_2 \cdot 3H_2O$ | 56.33 | 7.16 | | 56.08 | 7.18 | |

TABLE 2

(Infra-Red Spectra)

| Compound No. | Infra-Red maxima cm$^{-1}$ |
|---|---|
| 1 | 2950, 2840, 2610–2300, 1745, 1690, 1610, 1595, 1510 |
| 1a | 3010, 2940, 2860, 1740, 1610, 1595, 1510 |
| 1b | 2980, 2940, 2830, 1740, 1620, 1600, 1510 |
| 4 | 2950, 2850, 2630–2340, 1745, 1705, 1605, 1590, 1515 |
| 4a | 2900, 2810, 1740, 1610, 1590, 1505 |
| 4b | 2930, 2850, 1745, 1620, 1600, 1515 |
| 5 | 2940, 2850, 2630–2350, 1745, 1700, 1610, 1595, 1510 |
| 5a | 2930, 2820, 1735, 1605, 1595 |
| 5b | 2900, 2820, 1745, 1610, 1600, 1515 |
| 6 | 2940, 2860, 2630–2300, 1750, 1700, 1610, 1590, 1510 |
| 6a | 3000, 2950, 2850, 1740, 1610, 1600, 1510 |
| 6b | 2980, 2940, 2830, 1745, 1610, 1600, 1510 |
| 7 | 2940, 2850, 2640–2330, 1745, 1680, 1610, 1600, 1510 |
| 7a | 3000, 2940, 2870, 1745, 1610, 1600, 1510 |
| 10 | 3000, 2870, 2650–2400, 1755, 1690, 1620, 1600, 1515 |
| 10a | 3000, 2940, 2860, 1745, 1610, 1600, 1510 |
| 10b | 3000, 2950, 2830, 1740, 1620, 1600, 1510 |
| 11 | 2940, 2850, 2630–2310, 1745, 1705, 1605, 1595, 1510 |
| 11a | 2940, 2840, 1745, 1605, 1600, 1510 |
| 11b | 2940, 2850, 1745, 1610, 1510 |
| 12 | 2940, 2850, 2620–2330, 1750, 1705, 1610, 1595, 1515 |
| 12a | 2940, 2850, 1750, 1610, 1505 |
| 12b | 3000, 2940, 2850, 1745, 1610, 1510 |
| 13 | 2940, 2840, 2640–2340, 1745, 1705, 1610, 1595, 1505 |
| 13a | 2900, 2820, 1745, 1610, 1510, 1500 |
| 13b | 3000, 2940, 2850, 1745, 1610, 1510, 1500 |
| 14 | 2950, 2840, 2630–2300, 1745, 1705, 1610, 1595, 1510 |
| 14a | 2910, 2800, 1745, 1610, 1510 |
| 14b | 2990, 2940, 2850, 1745, 1610, 1510 |
| 15 | 2950, 2840, 2600–2280, 1745, 1705, 1605, 1595, 1510 |
| 15a | 2990, 2940, 2800, 1745, 1610, 1595, 1505, 1500 |
| 15b | 3000, 2940, 2850, 1745, 1610, 1510, 1505 |
| 16 | 2940, 2860, 2650–2340, 1750, 1710, 1615, 1590, 1515 |
| 16a | 2980, 2900, 1745, 1615, 1600, 1510 |
| 16b | 2970, 2880, 1750, 1615, 1600, 1515 |
| 17 | 2940, 2850, 2640–2310, 1750, 1715, 1615, 1595, 1515 |
| 17a | 2980, 2900, 1745, 1610, 1600, 1510 |
| 17b | 2950, 2870, 1745, 1610, 1510 |
| 18 | 2970, 2900, 2800, 2650–2330, 1745, 1705, 1610, 1590, 1500 |
| 18a | 2920, 2900, 2800, 1740, 1610, 1590, 1505 |
| 18b | 3000, 2900, 2810, 1740, 1610, 1505 |
| 18c | 3010, 2900, 2800, 1610, 1595, 1505 |
| 19 | 3460, 3000, 2960, 2850, 2630–2330, 1760, 1716, 1600, 1590, 1510, 1490 |
| 19b | 2990, 2940, 2860, 1755, 1600, 1510, 1490 |
| 20 | 3430, 2930, 2850, 2640–2350, 1750, 1710, 1600, 1590, 1490 |
| 20a | 3010, 2940, 2850, 1750, 1610, 1600, 1515, 1490 |
| 20b | 3000, 2950, 2870, 1750, 1600, 1510, 1490 |
| 21 | 2940, 2850, 2650–2300, 1740, 1705, 1610, 1590 |
| 21a | 2950, 2850, 1755, 1610, 1515 |
| 21b | 3000, 2950, 2850, 1745, 1610, 1510 |
| 22 | 2940, 2850, 2640–2320, 1745, 1705, 1605, 1595, 1510 |
| 22a | 3010, 2940, 2850, 1750, 1610, 1595, 1510 |
| 22b | 3000, 2940, 2850, 1745, 1610, 1505 |
| 23 | 3450, 3000, 2950, 2860, 2650–2350, 1760, 1720, 1650, 1595, 1520 |
| 23a | 2960, 2860, 1755, 1615, 1600, 1515 |
| 28 | 2940, 2880, 2650–2330, 1745, 1700, 1610, 1590, 1510 |
| 28a | 3000, 2880, 1740, 1615, 1600, 1520 |
| 28b | 2940, 2810, 1745, 1610, 1600, 1515 |

TABLE 3

| Compound No. | Rf | n.m.r. Spectra (p.p.m.) |
|---|---|---|
| 1a | 0.6 | δ(CHCl$_3$): 1.34–1.83 (6H, m, —(CH$_2$)$_3$), 2.26–3.44 (20H, m, 4 × ArCH$_2$—, 4 × CH$_2$ . N, 2 × CH$_2$ . COO), 3.62 (6H, s, 2 × C$_7$ArOCH$_3$), 3.87 (18H, s, 6 × ArOCH$_3$), 3.58–3.93 (2H, dd, 2 × ArCH.N), 3.97–4.16 (4H, m, 2 × COOCH$_2$), (2H, s, C$_8$Ar—H), 6.60–6.85 (8H, m, Ar—H). |
| 4a | 0.6 | δ(CDCl$_3$): 0.90 (3H, d, CH$_3$—CH), 1.32–1.91 (5H, m, CH$_2$—CH—CH$_2$), 2.23–3.39 (20H, m, 4 × ArCH$_2$, 4 × N—CH$_2$, 2 × CH$_2$COO), 3.56 (6H, s, 2 × C$_7$ArOCH$_3$), 4.05 (4H, t, 2 × CH$_2$COO), ca 4.31 (2H, dd, 2 × CH—N), 6.07 (2H, s, 2 × C$_8$Ar—H), 6.54–6.77 (8H, m, Ar—H). |
| 5a | 0.6 | δ(CDCl$_3$): 1.10–3.61 (30H, m, (CH$_2$)$_3$, 2 × CH—CH$_2$, 4 × Ar—CH$_2$, 4 × —N—CH$_2$, 2 × CH$_2$COO), 3.88 (6H, s, 2 × ArO—CH$_3$), 3.90 (12H, s, 4 × ArO—CH$_3$), 3.92 (6H, s, 2 × ArO—CH$_3$), 3.58–4.21 (6H, m, 2 ×0 CH—N, 2 × CO—O—CH$_2$), 6.56 (2H, s, Ar—H), 6.63 (2H, s, Ar—H), 6.85 (6H, s, Ar—H). |
| 6a | 0.6 | δ(CHCl$_3$): 1.23–1.78 (8H, m, —(CH$_2$)$_4$—), 2.31–3.36 (20H, m, 4 × ArCH$_2$—, 4 × —CH$_2$N, 2 × CH$_2$COO), 3.66 (6H, s, 2 × C$_7$ArOCH$_3$), 3.82 (6H, s, 2 × ArOCH$_3$), 3.86 (12H, s, 4 × ArOCH$_3$), 3.61–3.95 (2H, dd, 2 × ArCH . N), 3.98–4.14 (4H, m, 2 × COOCH$_2$), 6.14 (2H, s, C$_8$Ar—H), 6.61–6.84 (8H, m, Ar—H). |
| 7a | 0.6 | δ(CDCl$_3$): 1.50–1.83 (4H, m, —(CH$_2$)$_2$—), 2.25–3.45 (20H, m, 4 × ArCH$_2$—, 4 × CH$_2$N, 2 × CH$_2$COO), 3.65 (6H, s, 2 × C$_7$ArOCH$_3$), 3.88 (18H, s, 6 × ArOCH$_3$), 3.58–3.91 (2H, dd, ArCHN), 3.96–4.24 (4H, m, 2 × COOCH$_2$—) 6.17 (2H, s, C$_8$Ar—H), 6.59–6.87 (8H, m, Ar—H). |
| 10a | 0.6 | δ(CDCl$_3$): 1.90 (2H, t, —CH$_2$), 2.31–3.46 (20H, m, 4 × Ar—CH$_2$—, 4 × CH$_2$—N—, 2 × CH$_2$COO), 3.65 (6H, s, 2 × C$_7$ArOCH$_3$), 3.89 (18H, s, 6 × ArOCH$_3$), 3.61–3.94 (2H, dd, ArCH . N), 4.14 (2H, t, 2 × COOCH$_2$—), 6.16 (2H, s, 2 × C$_8$ArH), 6.59–6.88 (8H, m, Ar—H). |
| 11a | 0.6 | δ(CDCl$_3$): 2.30–3.50 (20H, m, 4 × ArCH$_2$, 4 × CH$_2$ . N, 2 × CH$_2$COO), 3.54 (6H, s, 2 × C$_7$ArOCH$_3$), 3.85 (24H, s, 8 × ArOCH$_3$), 3.63–3.90 (2H, dd, ArCH . N), 4.25 (4H, s, 2 × COOCH$_2$), 6.14 (2H, s, 2 × C$_8$ArH), 6.38 |

TABLE 3 -continued

| Compound No. | Rf | n.m.r. Spectra (p.p.m.) |
|---|---|---|
| 12a | 0.6 | (4H, s, Ar—H), 6.62 (2H, s, Ar—H). $\delta(CDCl_3)$: 2.25–3.49 (20H, m, 4 × ArCH$_2$, 4 × CH$_2$. N, 2 × CH$_2$COO), 3.68 (6H, s, 2C$_7$ArOCH$_3$), 3.78 (6H, s, 2 × ArOCH$_3$), 3.87 (12H, s, 4 × ArOCH$_3$), 3.58–3.90 (2H, dd, 2 × ArCH . N), 4.17 (4H, s, 2 × COOCH$_2$), 6.31 (2H, s, C$_8$Ar—H), 6.56–6.60 (4H, 2s, Ar—H), 7.08 (2H, s, Ar—H). |
| 13a | 0.6 | $\delta(CHCl_3)$: 2.25–3.45 (20H, m, 4 × ArCH$_2$), 4 × CH$_2$. N, 2 × CH$_2$COO), 3.70 (6H, s, 2 × C$_7$ArOCH$_3$), 3.85 (6H, s, 2 × C$_6$ArOCH$_3$), 3.60–3.91 (2H, dd, 2 × ArCH . N), 4.25 (4H, s, 2 × COOCH$_2$), 5.94 (4H, s, 2 × OCH$_2$O), 6.23 (2H, s, C$_8$Ar—H), 6.60–6.71 (8H, m, Ar—H). |
| 14a | 0.6 | $\delta(CDCl_3)$ 2.22–3.38 (20H, m, 4 × ArCH$_2$), 4 × CH$_2$. N, 2 × CH$_2$COO), 3.75 (6H, s, 2 × C$_7$ArOCH$_3$), 3.87 (6H, s, 2 × C$_6$ArOCH$_3$), 3.63–3.90 (2H, dd, 2 × ArCH . N), 4.22 (4H, s, 2 × COOCH$_2$), 6.30 (2H, s, C$_8$Ar—H), 6.60 (2H, s, C$_5$Ar—H), 6.89–7.42 (6H, m, Ar—H). |
| 15a | 0.6 | $\delta(CHCl_3)$: 2.28–3.43 (20H, m, 4 × ArCH$_2$, 4 × CH$_2$. N, 2 × CH$_2$COO), 3.62 (6H, s, 2 × C$_7$ArOCH$_3$), 3.71 (6H, s, 2 × ArOCH$_3$), 3.86 (6H, s, 2 × ArOCH$_3$), 3.59–3.88 (2H, dd, 2 × ArCH . N), 4.22 (4H, s, 2 × COOCH$_2$), 6.16 (2H, s, 2 × C$_8$Ar—H), 6.53–6.88 (8H, m, Ar—H). |
| 16a | 0.6 | $\delta(CDCl_3)$: 1.20–1.85 (10H, m, —(CH$_2$)$_5$—), 2.35–3.38 (20H, m, 4 × ARCH$_2$, 4 × CH$_2$. N, 2 × CH$_2$COO—), 3.67 (6H, s, 2 × C$_7$ArOCH$_3$), 3.85 (6H, s, ArOCH$_3$), 3.88 (6H, s, ArOCH$_3$), 3.91 (6H, s, ArOCH$_3$), 3.59–3.96 (2H, dd, ArCH . N) 4.0–4.19 (4H, m, 2 × COOCH$_2$—), 6.16 (2H, s, 2 × C$_8$Ar—H), 6.60–6.86 (8H, m, Ar—H). |
| 17a | 0.6 | $\delta(CDCl_3)$: 1.10–1.80, (12H, m, —(CH$_2$)$_6$—), 2.31–3.33 (20H, m, 4 × ArCH$_2$—, 4 × CH$_2$. N, 2 × CH$_2$COO), 3.64 (6H, s, 2 × C$_7$ArCCH$_3$), 3.83 (6H, s, 2 × ArOCH$_3$), 3.85 (6H, s, 2 × ArOCH$_3$), 3.88 (6H, s, 2 × ArOCH$_3$), 3.60–3.94 (2H, dd, 2 × ArCH . N), 3.96–4.18 (4H, m, 2 × COOCH$_2$—), 6.14 (2H, s, C$_8$Ar—H), 6.56–6.84 (8H, m, Ar—H). |
| 18a | 0.54 | $\delta(CHCl_3)$: 2.30–3.50 (20H, m, 4 × ArCH$_2$—, 4 × CH$_2$N, 2 × CH$_2$COO), 3.64 (6H, s, 2 × C$_7$ArOCH$_3$), 3.85 (18H, s, 6 × ArOCH$_3$), 3.70–4.11 (2H, dd, 2 × ArCH . N), 4.22 (4H, s, 2 × COOCH$_2$), 6.13 (2H, s, 2 × C$_8$Ar—H), 6.54–6.80 (8H, m, Ar—H). |
| 19a | 0.6 | $\delta(CDCl_3)$ 2.18–3.28 (20H, m, 4 × ArCH$_2$—, 4 × CH$_2$N, 2 × CH$_2$COO—), 3.83 (6H, s, ArOCH$_3$), 3.86 (6H, s, ArOCH$_3$), 3.65–3.91 (2H, dd, 2 × ArCH . N), 4.17 (4H, s, 2 × —COOCH$_2$), 5.87 (4H, s, 2 × OCH$_2$O), 6.34 (2H, s, 2 × C$_8$ArH), 6.53–6.84 (8H, m, Ar—H). |
| 20a | 0.6 | $\delta(CDCl_3)$: 1.27–1.78 (6H, m, —CH$_2$)—$_3$), 2.29–3.25 (20H, m, 4 × ArCH$_2$—, 4 × CH$_2$. N, 2 × CH$_2$COO), 3.87 (6H, s, ArOCH$_3$), 3.90 (6H, s, ArOCH$_3$), 3.68–3.88 (2H, dd, 2 × ArCH . N), 3.90–4.20 (4H, m, 2 × COOCH$_2$), 5.91 (4H, s, OCH$_2$O), 6.38 (2H, s, 2 × C$_8$ArH), 6.60–6.82 (8H, m, ArH). |
| 21a | 0.6 | $\delta(CDCl_3)$: 2.37–3.40 (20H, m, 4 × ArCH$_2$, 4 × CH$_2$. N, 2 × CH$_2$COO), 3.57 (6H, s, 2 × C$_7$ArOCH$_3$), 3.82 (6H, s, 2 × C$_6$ArOCH$_3$), 3.82 (6H, s, 2 × C$_6$ArOCH$_3$), 3.47–3.79 (2H, dd, 2 × ArCH . N), 4.10 (4H, s, 2 × COOCH$_2$), 6.07 (2H, s, C$_8$Ar—H), 6.57 (2H, s, C$_5$Ar—H), 7.12–7.32 (10H, m, Ar—H). |
| 22a | 0.6 | $\delta(CDCl_3)$ 2.29–3.45 (20H, m, 4 × ArCH$_2$, 4 × CH$_2$. N, 2 × CH$_2$COO) 3.62 (6H, s, 2 × C$_7$ArOCH$_3$), 3.78 (6H, s, 2 × ArOCH$_3$), 3.86 (6H, s, 2 × ArOCH$_3$), 3.54–3.86 (2H, dd, ArCH . N), 4.23 (4H, s, 2 × COOCH$_2$), 6.11 (2H, s, 2 × C$_8$Ar—H), 6.60 (2H, s, 2 × C$_5$Ar—H), 6.75–7.15 (8H, m, Ar—H). |
| 23a | 0.6 | $\delta(CDCl_3)$: 2.39–3.30 (20H, m, 4 × ArCH$_2$—, 4 × CH$_2$. N, 2 × CH$_2$COO), 3.59–3.85 (4H, m, 2 × —CH$_2$O), 3.67 (6H, s, C$_7$ArOCH$_3$), 3.86 (6H, s, 2 × ArOCH$_3$), 3.88 (6H, s, 2 × ArOCH$_3$), 3.91 (6H, s, 2 × ArOCH$_3$), 3.70–3.9 (2H, dd, ArCH . N), 4.15–4.41 (4H, m, 2 × CH$_2$OCO), 6.19, (2H, s, C$_8$Ar—H), 6.61–6.85 (8H, m, Ar—H). |
| 25a | 0.65 | $\delta(CDCl_3)$: 1.60–3.22 (26H, m, 4 × ArCH$_2$, 4 × N—CH$_2$, 3 × CH$_2$—CH$_2$—CH$_2$, 2 × CH$_2$—CO—O), 3.65 (6H, s, 2 × C$_7$ Ar—O—CH$_3$), 3.86 (18H, s, 6 × Ar—O—CH$_3$), 3.77–4.26 (6H, m, 2 × CO—O—CH$_2$, 2 × AR—CH—N), 6.14 (2H, s, 2 × C$_8$Ar—H), 6.56–6.80 (8H, m, Ar—H). |

What we claim is:

1. A compound of formula

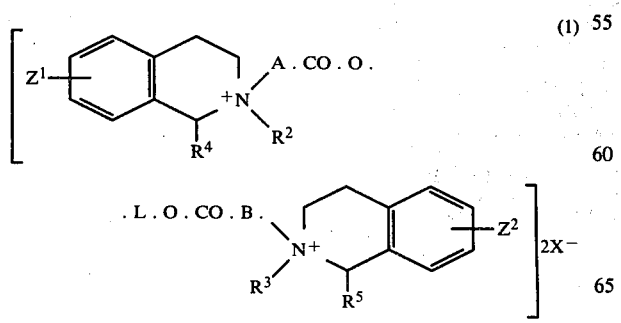

(1)

wherein $Z^1$ and $Z^2$ are the same or different and each represents a methylenedioxy substituent, or up to three methoxy substituents:

$R^2$ and $R^3$ are the same or different and each is alkyl having 1–3 carbon atoms, prop-2-enyl or prop-2-ynyl;

$R^4$ and $R^5$ are the same or different and each is a benzyl or phenethyl group wherein the phenyl ring is unsubstituted or is substituted by one or more of halogen, alkoxy having 1 to 3 carbon atoms and methylenedioxy;

A and B are the same or different and each is an alkylene radical containing 1, 2 or 3 carbon atoms;

L is an alkylene chain having from 2 to 12 carbon atoms or is a group —$L^1$.0.$L^2$—wherein each of $L^1$ and $L^2$ is alkylene having at least two carbon atoms and taken together L¹ and L² have upto 11 carbon atoms; and X⁻ is an anion.

2. A compound as claimed in claim 1 wherein each of A and B is —CH₂.CH₂—, each of R² and R³ is methyl, each of R⁴ and R⁵ is mono-, di- or tri- methyoxybenzyl, each of Z¹ and Z² is 6,7-dimethoxy and L is alkylene having 2 to 8 carbon atoms.

3. A compound as claimed in claim 1 which is N,N'-dimethyl-N,N'-4,10-dioxa-3,11-dioxotridecylene-1,13-bis-tetrahydropapaverinium di-iodide.

4. A compound as claimed in claim 1 wherein L is straight pentylene.

5. A compound as claimed in claim 1 wherein each of R⁴ and R⁵ is 3,4-dimethoxybenzyl.

6. A compound as claimed in claim 1 wherein X⁻ is a pharmaceutically acceptable anion.

7. A compound as claimed in claim 1 wherein the compound has a solubility in water at room temperature of 20mg/ml or more.

8. A compound as claimed in claim 1 wherein X⁻ is chloride, bromide, iodide, sulphonate, methanesulphonate, benzenesulphonate, p-toluenesulphonate, nitrobenzenesulphonate, naphthalenesulphonate, or tartrate.

9. A compound as claimed in claim 1 wherein X⁻ is the anion of an organic acid.

10. A compound as claimed in claim 1 wherein X⁻ is benzenesulphonate, p-toluenesulphonate, naphthalene-1-sulphonate or naphthalene-2-sulphonate.

11. A compound as claimed in claim 1 which is a N,N'-dimethyl-N,N'-7-methyl-4,10-dioxa-3,11-dioxotridecylene-1,13-bis-tetrahydropapaverinium, N,N'-dimethyl-N,N'-4,10-dioxa-3,11-dioxotridecylene-1,13-bis-(1',2',3',4'-tetrahydro-6',7'-dimethoxy-1-[2-(3",4"-dimethoxyphenyl)ethyl-]isoquinolinium), N,N'-dimethyl-N,N'-4,8-dioxa-3,9-dioxoundecylene-1,11-bis-tetrahydropapaverinium, N,N'-dimethyl-N,N'-4,7-dioxa-3,8-dioxodecylene-1,10-bis-[1',2',3',4'-tetrahydro-6',7'-dimethoxy-1-(3",4",5"-trimethoxybenzyl)isoquinolinium], N,N'-dimethyl-N,N'-4,7-dioxa-3,8-dioxodecylene-1,10-bis[1',2',3',4'-tetrahydro-6',7'-dimethoxy -1-(2-bromo-4",5"-dimethoxybenzyl)isoquinolinium, N,N'-dimethyl-N,N'-4,7-dioxa-3,8-dioxodecylene-1,10-bis[1',2',3',4'-tetrahydro-6',7'-dimethoxy-1-(3",4"-methylenedioxybenzyl)isoquinolinium, N,N'-dimethyl-N,N'-4,7-dioxa-3,8-dioxodecylene-1,10-bis[1',2',3',4'-tetrahydro-6',7'-dimethoxy-1-(3",4"-dichlorobenzyl)isoquinolinium, N,N'-dimethyl-N,N'-4,7-dioxa-3,8-dioxodecylene-1,10-bis[1',2',3',4'-tetrahydro-6',7'-dimethoxy-1-(2",5"-dimethoxybenzyl)isoquinolinium], N,N'-dimethyl-N,N'-4,13-dioxa-3,14-dioxohexadecylene-1,16-bis-tetrahydropapaverinium, N,N'-dimethyl-N,N'-4,7-dioxa-3,8-dioxodecylene-1,10-bis-(±)-tetrahydropapaverinium, N,N'-dimethyl-N,N'-4,7-dioxa-3,8-dioxodecylene-1,10-bis-(±)-tetrahydropapaverinium, N,N'-dimethyl-N,N'-4,7-dioxa-3,8-dioxodecylene-1,10-bis-[1',2',3',4'-tetrahydro-1'-(3",4"-dimethoxybenzyl)-6',7'-methylenedioxyisoquinolinium], N,N'-dimethyl-N,N'-4,10-dioxa-3,11-dioxotridecylene-1,13-bis[1',2',3',4'-tetrahydro-1'-(3",4"-dimethoxybenzyl)-6',7'-methylenedioxyisoquinolinium], N,N'-dimethyl-N,N'-4,7-dioxa-3,8-dioxodecylene-1,10-bis(1',2',3',4'-tetrahydro-6',7'-dimethoxy-1'-benzylisoquinolinium, N,N'-dimethyl-N,N'-4,7-dioxa-3,8-dioxodecylene-1,10bis[1',2',3',4'-tetrahydro-6',7'-dimethoxy-1'-(4"-methoxybenzyl)isoquinolinium], N,N'-dimethyl-N,N'-4,7,10-trioxa-3,11-dioxotridecylene-1,13 -bis-tetrahydropapaverinium, meso-N,N'-dimethyl-N,N'-4,7-dioxa-3,8-dioxodecylene-1,10-bis-tetrahydropapaverinium, or N,N'-dimethyl-N,N'-5,9-dioxa-4,10-dioxotridecylene-1,13bis-tetrahydropapaverinium salt.

12. A compound as claimed in claim 1 which is a N,N'-dimethyl-N,N'-4,9-dioxa-3,10-dioxododecylene-1,12-bis-(±)-tetrahydropapaverinium, or N,N'-dimethyl-N,N'-4,12-dioxa-3,13-dioxopentadecylene-1,15-bis-tetrahydropapaverinium salt.

13. A compound as claimed in claim 1 which is a N,N'-dimethyl-N,N'-4,11-dioxa-3,12-dioxotetradecylene-1,14-bis-tetrahydropapaverinium salt.

14. A compound as claimed in claim 1 which is a N,N'-dimethyl-N,N'-4,10-dioxa-3,11-dioxotridecylene-1,13-bis-tetrahydropapaverinium, N,N'-dimethyl-N,N'-4,10-dioxa-3,11-dioxotridecylene-bis-D-(—)-tetrahydropapaverinium, o N,N'-dimethyl-N,N'-4,10-dioxa-3,11-dioxotridecylene-1,13-bis-L-(+)-tetrahydropapaverinium or meso N,N'-dimethyl-N,N'-4,10-dioxo-3,11-tridecylene-1,13-bis-tetrahydropapverinium salt.

15. A compound as claimed in 1 wherein the compound is in the form of a substantially dry powder.

16. A pharmaceutical composition comprising a compound of formula (I)

$$\left[ Z^1 \underset{R^4}{\overset{+N}{\diagdown}} \overset{A.CO.O.}{\underset{R^2}{\diagdown}} \right.$$

$$\left. \underset{R^3}{\overset{L.O.CO.B.}{\diagdown}} \underset{R^5}{\overset{N^+}{\diagdown}} Z^2 \right] 2X^-$$

in amount sufficient to effect neuromuscular paralysis wherein

Z¹ and Z² are the same or different and each represents a methylenedioxy substituent, or up to three methoxy substituents;

R² and R³ are the same or different and each is alkyl having 1–3 carbon atoms, prop-2-enyl or prop-2-ynyl;

R⁴ and R⁵ are the same or different and each is a benzyl or phenethyl group wherein the phenyl ring is optionally substituted by one or more of halogen, alkoxy having 1 to 3 carbon atoms and methylenedioxy;

A and B are the same or different and each is an alkylene radical containing 1, 2 or 3 carbon atoms;

L is an alkylene chain having from 2 to 12 carbon atoms or is a group —L¹.O.L²— wherein each of L¹ and L² is alkylene having at least two carbon atoms and taken together L¹ and L² have upto 11 carbon atoms; and X⁻is a pharmaceutically acceptable anion;

in association with a pharmaceutically acceptable carrier.

17. A composition as claimed in claim 16 wherein in formula (I) each of A and B is —CH$_2$.CH$_2$—, each of R$^2$ and R$^3$ is methyl, each of R$^4$ and R$^5$ is mono-, di- or trimethoxybenzyl, each of Z$^1$ and Z$^2$ is 6,7-dimethoxy and L is alkylene having 2 to 8 carbon atoms.

18. A composition as claimed in claim 16 wherein in formula (I) each of R$^4$ and R$^5$ is 3,4-dimethoxybenzyl and L is straight butylene or pentylene.

19. A composition as claimed in claim 16 wherein the compound is N,N'-dimethyl-N,N'-4,10-dioxa-3,11-dioxotridecylene-1,13-bis-tetrahydropapaverinium dibesylate.

20. A composition as claimed in claim 16 wherein the compound is N,N'-dimethyl-N,N'-4,10-dioxa-3,11-dioxotridecylene-1,13-bis-tetrahydropapaverinium di-iodide.

21. A composition as claimed in claim 16 in the form of an injectable solution.

22. A composition as claimed in claim 16 comprising from 5 to 50 mg of a compound of formula (I) per milliliter.

23. A composition as claimed in claim 16 in the form of a unit dose comprising from 40 to 60 mg of a compound of formula (I).

24. A method of inducing neuromuscular paralysis in a mammal comprising the systemic administration to said mammal of an effective neuromuscular paralysing amount of a compound of formula (I)

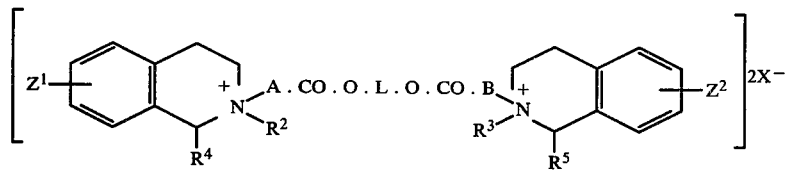

wherein
Z$^1$ and Z$^2$ are the same or different and each represents a methylenedioxy substituent, or up to three methoxy substituents;
R$^2$ and R$^3$ are the same or different and each is alkyl having 1–3 carbon atoms, prop-2-enyl or prop-2-ynyl;
R$^4$ and R$^5$ are the same or different and each is a benzyl or phenethyl group wherein the phenyl ring is optionally substituted by one or more of halogen, alkoxy having 1 to 3 carbon atoms and methylenedioxy;
A and B are the same or different and each is an alkylene radical containing 1, 2 or 3 carbon atoms;
L is an alkylene chain having from 2 to 12 carbon atoms or is a group —L$^1$.O.L$^2$—wherein each of L$^1$ and L$^2$ has at least two carbon atoms and taken together L$^1$ and L$^2$ have up to eleven carbon atoms; and
X$^-$ is a pharmaceutically acceptable anion;
in association with a pharmaceutically acceptable carrier.

25. A method as claimed in claim 24 wherein in formula (I) each of A and B is —CH$_2$.CH$_2$—, each of R$^2$ and R$^3$ is methyl, each of R$^4$ and R$^5$ is mono-, di- or trimethoxybenzyl, each of Z$^1$ and Z$^2$ is 6,7-dimethoxy and L is alkylene having 2 to 8 carbon atoms.

26. A method as claimed in claim 24 wherein formula (I) each of R$^4$ and R$^5$ is 3,4-dimethoxybenzyl and L is straight butylene or pentylene.

27. A method as claimed in claim 24 wherein the compound is N,N'-dimethyl-N,N'-dioxa-3,11-dioxotridecylene-1,13-bis-tetrahydropapaverinium di-iodide.

28. A method as claimed in claim 24 wherein—the compound of formula (I) is a N,N'-dimethyl-N,N'-4,10-dioxa-3,11-dioxotridecylene-1,13-bis-tetrahydropapaverinium salt.

29. A method as claimed in claim 24 wherein the mammal is man.

30. A method as claimed in claim 24 wherein intravenous, subcutaneous or intramuscular administration is employed.

31. A method as claimed in claim 24 wherein the compound of formula (I) is administered at a dose of from 0.1 to 4.0 mg per kg bodyweight of said mammal.

32. A method as claimed in claim 31 wherein the dose is from 0.25 to 1.0 mg/kg.

33. A compound of formula (III)

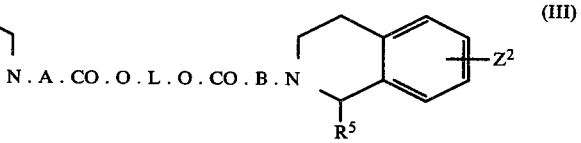 (III)

wherein
Z$^1$ and Z$^2$ are the same or different and each represents a methylenedioxy substituent, or up to three methoxy substituents;
R$^4$ and R$^5$ are the same or different and each is a benzyl or phenethyl group wherein the phenyl ring is unsubstituted or substituted by one or more of halogen, alkoxy having 1 to 3 carbon atoms and methylenedioxy;
A and B are the same or different and each is an alkylene radical containing 1, 2 or 3 carbon atoms; and
L is an alkylene chain having 2 to 12 carbon atoms or is a group —L$^1$.O.L$^2$—wherein each of L$^1$ and L$^2$ is alkylene having at least two carbon atoms and taken together L$^1$ and L$^2$ having up to 11 carbon atoms; or the corresponding dioxalate salt thereof.

34. A compound of formula (IX)

G.CO.O.L.O.CO.G$^2$ (IX)

wherein
L is an alkylene chain having from 2 to 12 carbon atoms or is a group —L$^1$.O.L$^2$—wherein each of L$^1$ and L$^2$ is alkylene having at least two carbon atoms and taken together L$^1$ and L$^2$ having up to 11 carbon atoms;

G and $G^2$ are the same or different and each is a group—$C(J^1)=CHJ^2$ or a reactive ester derivative of the group—J.OH wherein J is alkylene having 1 to 3 carbon atoms, one of $J^1$ and $J^2$ is hydrogen and the other of $J^1$ and $J^2$ is hydrogen or methyl.

or G is a group as defined above and $G^2$ is a group

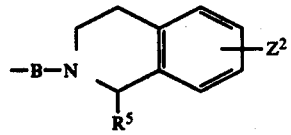

wherein $Z^2$ represents a methylenedioxy substituent, or up to three methoxy substituents;

$R^5$ is a benzyl or phenethyl group wherein the phenyl ring is unsubstituted or substituted by one or more of halogen, alkoxy having 1 to 3 carbon atoms and methylenedioxy; and B is an alkylene radical containing 1, 2 to 3 carbon atoms.

35. N,N'-Dimethyl-N,N'-4,10-dioxa-3,11-dioxotridecylene-1,13-bis-tetrahydropapaverinium dibesylate.

36. N,N'-Dimethyl-N,N'-4,10-dioxa-3,11-dioxotridecylene-1,13-bis-tetrahydropapaverinium ditosylate.

37. N,N'-Dimethyl-N,N'-4,10-dioxa-3,11-dioxotridecylene-1,13-bis-tetrahydropapaverinium dinaph-1-sylate.

38. N,N'-Dimethyl-N,N'-4,10-dioxa-3,11-dioxotridecylene-1,13-bis-tetrahydropapaverinium dinaph-2-sylate.

39. N,N'-dimethyl-N,N'-4,10-dioxa-3,11-dioxotridecylene-1,13-bis-tetrahydropapaverinium dimesylate.

40. The composition of claim 16 in which the compound is N,N'-dimethyl-N,N'-4,10-dioxa-3,11-dioxotridecylene-1,13-bis-tetrahydropapaverinium dimesylate.

41. The method of claim 24 in which the compound is N,N'-dimethyl-N,N'-4,10-dioxa-3,11-dioxotridecylene-1,13-bis-tetrahydropapaverinium dimesylate.

42. Pharmaceutically acceptable salt of the N,N'-dimethyl-N,N'-4,10-dioxa-3,11-dioxotridecylene-1,13-bis-tetrahydropapaverinium cation.

43. A method as claimed in claim 24 in which the compound is N,N'-dimethyl-N,N'-4,10-dioxa-3,11-dioxotridecylene-1,13-bis-tetrahydropapaverinium dibesylate.

* * * * *

U NITED STATES PATENT AND TRADEMARK OFFICE
CERTIFICATE OF CORRECTION

PATENT NO. : 4,179,507
DATED : Dec. 18, 1979
INVENTOR(S) : John B. Stenlake, et al., It is certified that error appears in the above-identified patent and that said Letters Patent are hereby corrected as shown below:

Columns 3 and 4, formula (II)
Delete "$(CH_2)_2.CO.O.(CH_2)_2.O.CO.(CH_2)_2$" and insert --- $(CH_2)_2.CO.O.(CH_2)_n.O.CO.(CH_2)_2$ ---

Columns 9 and 10, delete "$(CH_2)_2.CO.O.(CH_2)_2.O.CO.(CH_2)_2$"
$(CH_2)_2.CO.O.(CH_2)_5.O.CO.(CH_2)_2$ ---

Columns 13 and 14, example 26, delete "$(CH_2)_2.CO.O.(CH_23)_2.O.CO.(CH_2)_2$" and insert --- $(CH_2)_2.CO.O.(CH_2)_5.O.CO.(CH_2)_2$ ---

Columns 16 and 17, in the empirical formulae in Table 1

"COMPOUND NO."

| | |
|---|---|
| "2b" | after "$O_{18}$" insert --- $S_2$ --- |
| "24" | delete "$O_2$" and insert --- $O_{20}$ --- |
| "24c" | insert ---$O_{12}$ --- |
| "25" | delete "$O_2$" and insert --- $O_{20}$ --- |
| "26" | delete "$O_2$" and insert --- $O_{20}$ --- |
| "26b" | delete "$O_8$" and insert --- $O_{18}$ --- |

Signed and Sealed this

Twenty-ninth Day of July 1980

[SEAL]

Attest:

SIDNEY A. DIAMOND

Attesting Officer     Commissioner of Patents and Trademarks